United States Patent
Marushima et al.

(10) Patent No.: US 11,801,486 B2
(45) Date of Patent: Oct. 31, 2023

(54) SYNTHETIC PRODUCT PRODUCTION SYSTEM AND CARBON DIOXIDE TREATMENT SYSTEM

(71) Applicant: MITSUBISHI HEAVY INDUSTRIES, LTD., Tokyo (JP)

(72) Inventors: Shinya Marushima, Yokohama (JP); Tadateru Tanioka, Yokohama (JP); Kazunori Fujita, Yokohama (JP); Yoshimasa Ando, Yokohama (JP); Takahiro Kamo, Yokohama (JP); Kenichi Irie, Yokohama (JP); Atsushi Tsutsumi, Yokohama (JP)

(73) Assignee: MITSUBISHI HEAVY INDUSTRIES, LTD., Tokyo (JP)

(*) Notice: Subject to any disclaimer, the term of this patent is extended or adjusted under 35 U.S.C. 154(b) by 0 days.

(21) Appl. No.: 17/642,767

(22) PCT Filed: Sep. 16, 2020

(86) PCT No.: PCT/JP2020/035148
§ 371 (c)(1),
(2) Date: Mar. 14, 2022

(87) PCT Pub. No.: WO2021/054378
PCT Pub. Date: Mar. 25, 2021

(65) Prior Publication Data
US 2022/0331773 A1    Oct. 20, 2022

(30) Foreign Application Priority Data
Sep. 17, 2019   (JP) .................... 2019-168662

(51) Int. Cl.
*B01J 19/00*   (2006.01)
*B01J 12/00*   (2006.01)
*C07C 1/12*    (2006.01)
*C10L 3/08*    (2006.01)

(52) U.S. Cl.
CPC ........... *B01J 19/0033* (2013.01); *B01J 12/00* (2013.01); *C07C 1/12* (2013.01);
(Continued)

(58) Field of Classification Search
CPC ........ B01J 19/0033; B01J 19/00; B01J 12/00; B01J 2219/00182; B01J 2219/00162;
(Continued)

(56) References Cited

U.S. PATENT DOCUMENTS 2,902,434 A * 9/1959 Burton .................... C10G 35/22
                                                     208/138
9,108,894 B1   8/2015 Foody et al.
(Continued)

FOREIGN PATENT DOCUMENTS

JP   H11-46460 A      2/1999
JP   2008-247636 A   10/2008
(Continued)

OTHER PUBLICATIONS

International Search Report dated Nov. 24, 2020 issued in counterpart application No. PCT/JP2020/035148, with English translation. (14 pages).

(Continued)

*Primary Examiner* — Lessanework Seifu
(74) *Attorney, Agent, or Firm* — WHDA, LLP (57) ABSTRACT

A synthetic product production system is provided with: a synthesis plant for producing a synthetic product by synthesizing a hydrogen-containing gas and carbon dioxide; and a carbon dioxide supply line for supplying the carbon dioxide to the synthesis plant from a recovery and storage plant including a recovery device for recovering the carbon dioxide from a carbon dioxide-containing gas and an injection facility for fixing the recovered carbon dioxide into a stratum.

7 Claims, 5 Drawing Sheets

(52) U.S. Cl.
CPC ....... *B01J 2219/00182* (2013.01); *C10L 3/08* (2013.01); *Y02E 20/32* (2013.01); *Y02E 50/30* (2013.01); *Y02P 20/151* (2015.11)

(58) Field of Classification Search
CPC .... B01J 2219/00164; C10L 3/08; C07C 1/12; C07C 41/01; C07C 29/151; C07C 31/04; Y02P 20/141; Y02P 20/151; Y02P 20/32; Y02E 50/30
See application file for complete search history.

(56) References Cited

U.S. PATENT DOCUMENTS

| | | | |
|---|---|---|---|
| 9,885,257 B2 * | 2/2018 | Bergins | C07C 29/00 |
| 2011/0229382 A1 * | 9/2011 | Frydman | F01K 23/068 422/621 |
| 2012/0226080 A1 * | 9/2012 | Meyer-Pittroff | C07C 29/50 422/162 |
| 2014/0123672 A1 * | 5/2014 | Huntington | F02C 3/34 60/39.23 |

FOREIGN PATENT DOCUMENTS

| | | |
|---|---|---|
| JP | 2011-246525 A | 12/2011 |
| JP | 2013-010697 A | 1/2013 |
| JP | 2018-008940 A | 1/2018 |

OTHER PUBLICATIONS

Notification of Transmittal of Translation of the International Preliminary Report on Patentabililty (Form PCT/IB/338) issued in counterpart International Application No. PCT/JP2020/035148 dated Mar. 31, 2022 with Forms PCT/IB/373, PCT/IB/326 and PCT/ISA/237. (14 pages).

Ijima et al., "Fuel Gas CO2 Recovery Utilization, Disposal and Business Development", Mitsubishi Heavy Industries Technical Review, 2002, vol. 39, No. 5, pp. 286-289, cited in ISR dated Nov. 24, 2020. (4 pages).

Fujieda et al., "Under the Scenes of our Lives, High-pressure pump—CO2 Injection Pump", Ebara Engineering Review, 2016, No. 252, pp. 8-12, cited in ISR dated Nov. 24, 2020. (5 pages).

Kanno et al., "Technology for Pressurizing and Transporting CO2", Ebara Engineering Review, 2010, No. 226, pp. 5-10, cited in ISR dated Nov. 24, 2020. (6 pages).

The Examination Report dated Feb. 13, 2023, issued in counterpart GB application No. 2203242.9.

Iijima, Masaki et al. "Fuel Gas CO2 Recovery Utilization, Disposal and Business Development," Mitsubishi Heavy Industries Technical Review, vol. 40, No. 1, pp. 1-5, Jan. 2003; Cited in GB Office Action dated Feb. 13, 2023. (4 pages).

* cited by examiner

FIG. 5

SYNTHETIC PRODUCT PRODUCTION SYSTEM AND CARBON DIOXIDE TREATMENT SYSTEM

TECHNICAL FIELD

The present disclosure relates to a synthetic product production system and a carbon dioxide treatment system.

BACKGROUND

As a measure to prevent global warming, it is required to reduce carbon dioxide emissions associated with the use of fossil fuels. One proposed solution is to recover carbon dioxide from a carbon dioxide-containing gas and use it as a resource of a synthetic product (fuel, chemical materials, etc.). In this case, it is possible to reduce carbon dioxide emissions to the atmosphere. For example, Patent Document 1 discloses a system for producing fuel by combining hydrogen obtained by electrolysis of water or seawater with carbon dioxide separated from exhaust gas of a power generation facility.

Another solution focuses on the treatment of carbon dioxide rather than the use of carbon dioxide. For example, Patent Document 2 discloses a carbon dioxide recovery device for recovering carbon dioxide from a carbon dioxide-containing gas by using a PSA device and a carbon dioxide separation membrane. The hydrogen-enriched gas after recovering carbon dioxide is used as product hydrogen. On the other hand, the recovered carbon dioxide is transported to another place in a liquefied state and stored underground or in the sea at the transport destination.

CITATION LIST

Patent Literature

Patent Document 1: JPH11-46460A
Patent Document 2: JP2008-247636A

SUMMARY

Problems to be Solved

As in Patent Document 1, if a dedicated carbon dioxide recovery device (i.e., a carbon dioxide recovery device dedicated to a synthesis plant) is provided in order to recover only carbon dioxide used for the production of a synthetic product, the facility cost increases. As a result, the production cost of the synthetic product also increases. Patent Document 2 also does not disclose a solution to solve such problems.

In view of the above, an object of the present disclosure is to provide a synthetic product production system and a carbon dioxide treatment system which do not require a carbon dioxide recovery device dedicated to a synthesis plant and can reduce the facility cost.

Solution to the Problems

A synthetic product production system according to the present disclosure comprises: a synthesis plant for producing a synthetic product by synthesizing a hydrogen-containing gas and carbon dioxide; and a carbon dioxide supply line for supplying the carbon dioxide to the synthesis plant from a recovery and storage plant including a recovery device for recovering the carbon dioxide from a carbon dioxide-containing gas and an injection facility for fixing the recovered carbon dioxide into a stratum.

A carbon dioxide treatment system according to the present disclosure comprises: the above-described synthetic product production system; a recovery and storage plant including a recovery device for recovering carbon dioxide from a carbon dioxide-containing gas and an injection facility for fixing the recovered carbon dioxide into a stratum; a power generation facility configured to generate power by combustion of an off-gas from the recovery device of the recovery and storage plant; and an unreacted gas supply line for supplying at least part of a discharged unreacted gas from a pipe for recirculating the unreacted gas to the power generation facility.

Advantageous Effects

The present disclosure provides a synthetic product production system and a carbon dioxide treatment system which do not require a carbon dioxide recovery device dedicated to a synthesis plant and can reduce the facility cost.

DETAILED DESCRIPTION

Embodiments will now be described in detail with reference to the accompanying drawings. It is intended, however, that unless particularly specified, dimensions, materials, shapes, relative positions and the like of components described in the embodiments shall be interpreted as illustrative only and not intended to limit the scope of the present invention.

For instance, an expression of relative or absolute arrangement such as "in a direction", "along a direction", "parallel", "orthogonal", "centered", "concentric" and "coaxial" shall not be construed as indicating only the arrangement in a strict literal sense, but also includes a state where the arrangement is relatively displaced by a tolerance, or by an angle or a distance whereby it is possible to achieve the same function.

For instance, an expression of an equal state such as "same" "equal" and "uniform" shall not be construed as indicating only the state in which the feature is strictly equal, but also includes a state in which there is a tolerance or a difference that can still achieve the same function.

Further, for instance, an expression of a shape such as a rectangular shape or a cylindrical shape shall not be construed as only the geometrically strict shape, but also includes a shape with unevenness or chamfered corners within the range in Which the same effect can be achieved.

On the other hand, an expression such as "comprise", "include", "have", "contain" and "constitute" are not intended to be exclusive of other components.

FIGS. 1 to 5 are each a schematic configuration diagram of a carbon dioxide treatment system 1 (1A, 1B, 1C, 1D, 1E) according to an embodiment of the present disclosure. For example, as shown in FIGS. 1 to 5, the carbon dioxide treatment system 1 (1A, 1B, 1C, 1D, 1E) includes a synthetic product production system 2 and a recovery and storage plant 3.

As shown in FIGS. 1 to 5, the synthetic product production system 2 includes a synthesis plant 10 for producing a synthetic product by synthesizing a hydrogen-containing gas and carbon dioxide, and a carbon dioxide supply line 11 for supplying carbon dioxide to the synthesis plant 10 from the recovery and storage plant 3. The synthesis plant 10 is configured to produce at least one of methanol, methane, or dimethyl ether as the synthetic product. Further, the synthesis plant 10 drains water as a by-product of the synthetic product.

Figure 2:
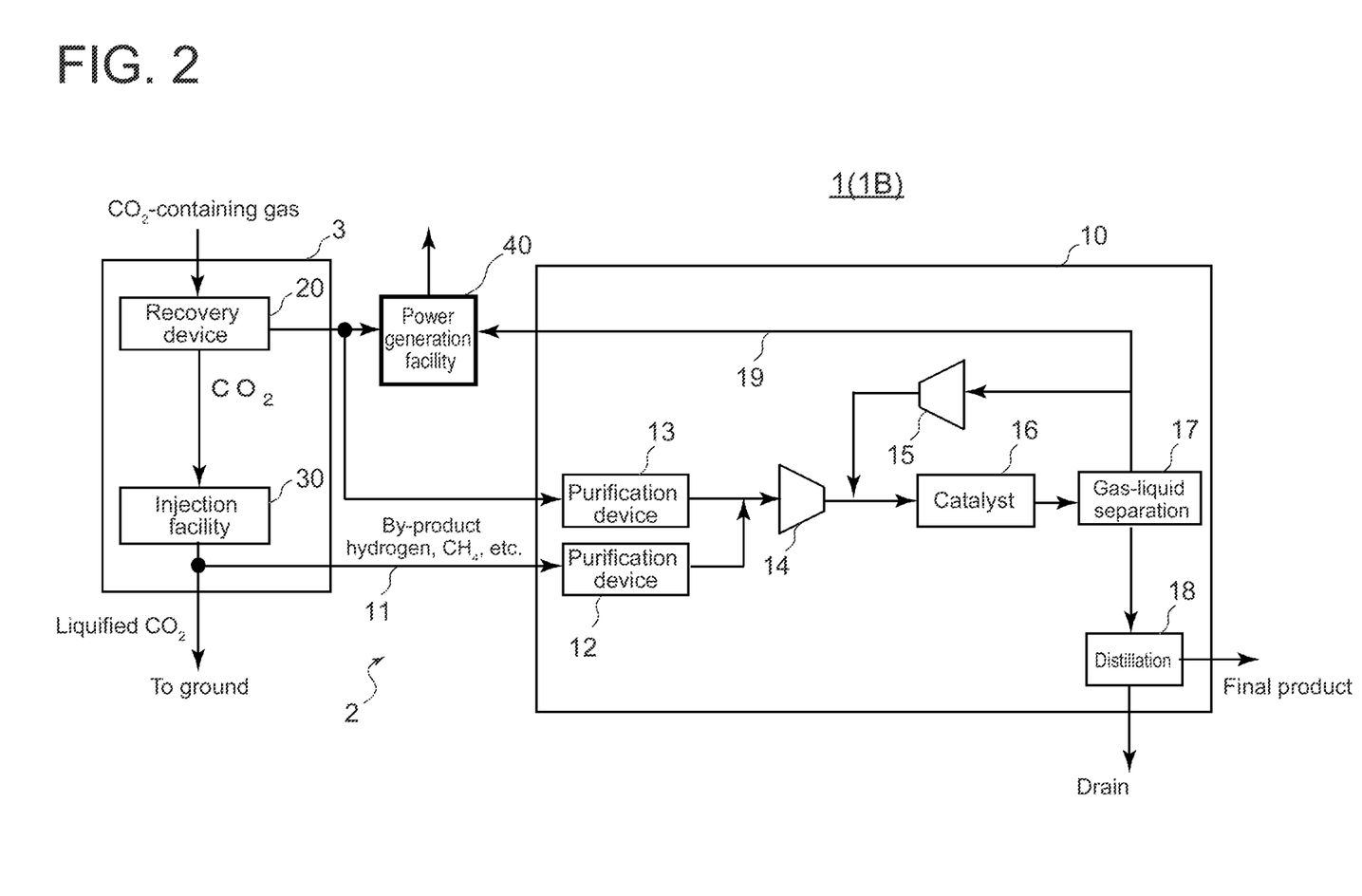
FIG. 2 is a schematic configuration diagram of a carbon dioxide treatment system according to an embodiment.
Figure 3:
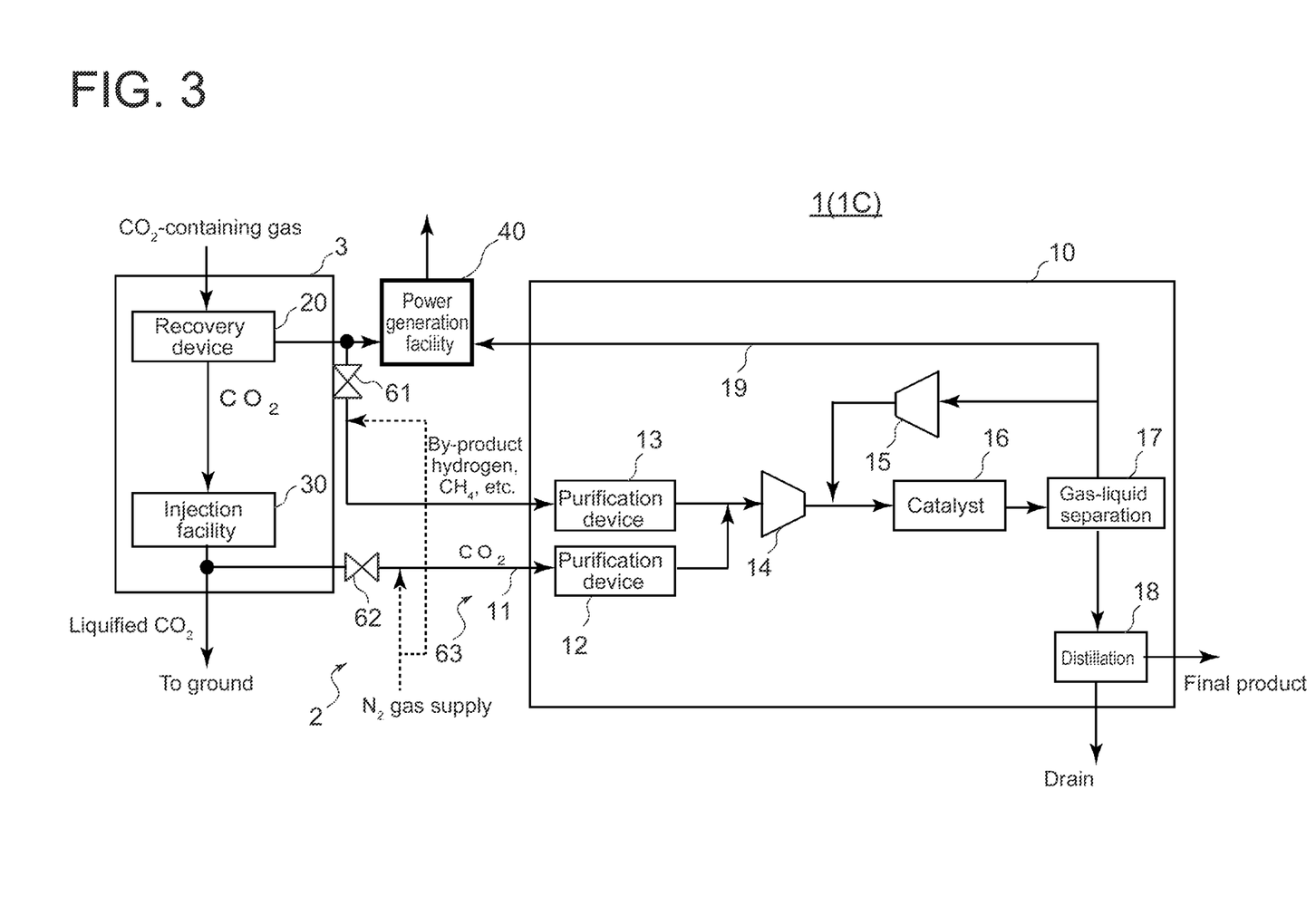
FIG. 3 is a schematic configuration diagram of a carbon dioxide treatment system according to an embodiment.

In some embodiments, for example, as shown in FIGS. 2 and 3, the synthesis plant 10 may include a purification device 12 for purifying carbon dioxide compressed by an injection facility 30 of the recovery and storage plant 3 and a purification device 13 for purifying hydrogen from off-gas after a recovery device 20 of the recovery and storage plant 3 recovers carbon dioxide from a carbon dioxide-containing gas.

Figure 4:
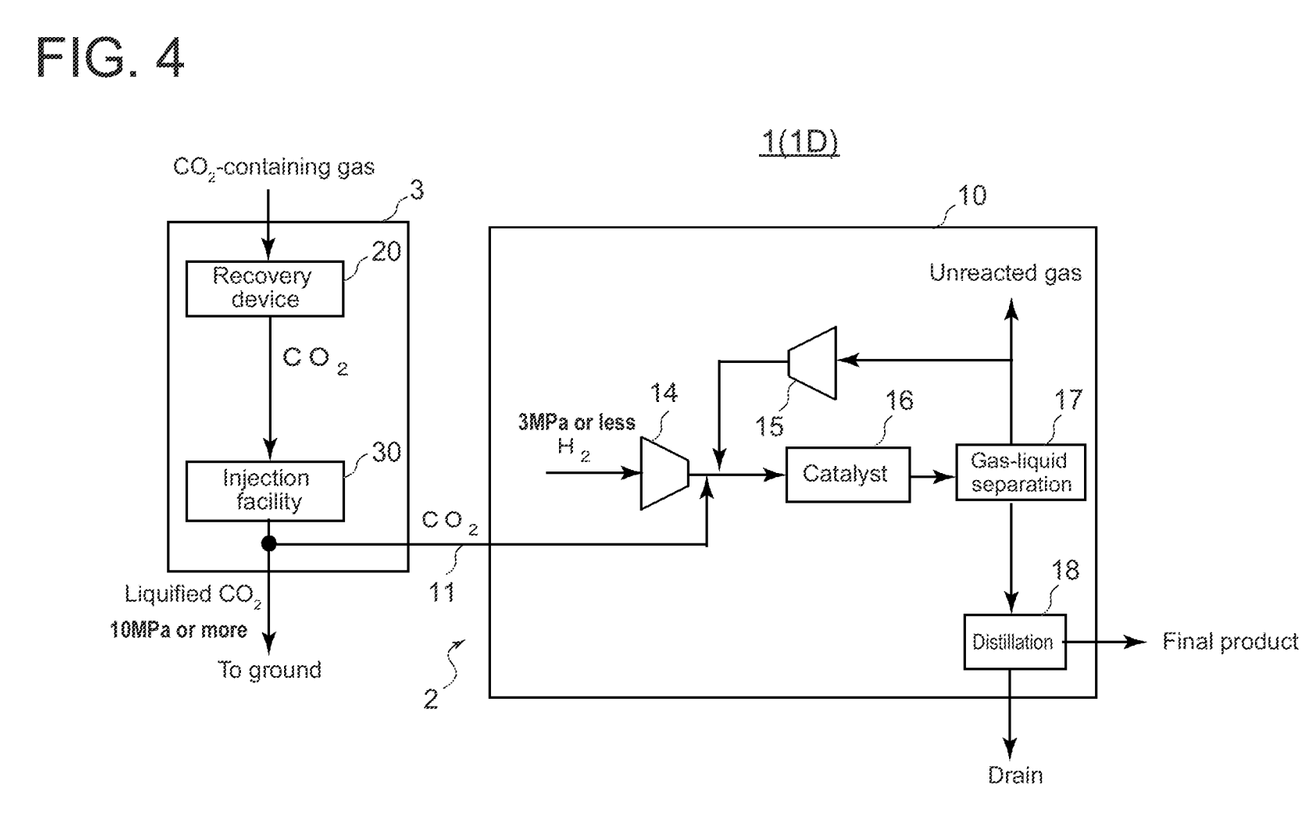
FIG. 4 is a schematic configuration diagram of a carbon dioxide treatment system according to an embodiment.

The synthesis plant 10 includes a catalyst 16 for chemically reacting hydrogen and carbon dioxide to produce the synthetic product, and a gas-liquid separation device 17 for performing gas-liquid separation of the synthetic product produced by the chemical reaction. The synthesis plant 10 may include a compressor 15 configured to compress an unleaded gas separated by the gas-liquid separation device 17 and supply it to the upstream side of the catalyst 16. In other words, the unreacted gas may be recirculated. Further, for example, as shown in FIGS. 2, 3, and 4, the synthesis plant 10 includes a distillation device 18 configured to distill a liquid discharged from the gas-liquid separation device 17 and separate it into water and a final product (high-purity synthetic product).

The synthesis plant 10 may include a raw material supply compressor 14 upstream of the catalyst 16. For example, the raw material supply compressor 14 may be disposed downstream of the purification devices 12, 13 and may be configured to compress a mixture of carbon dioxide and hydrogen as shown in FIGS. 2 and 3, or may be configured to compress hydrogen (hydrogen-containing gas before mixing with carbon dioxide) as shown in FIG. 4.

The recovery and storage plant 3 includes a recovery device 20 for recovering carbon dioxide from a carbon dioxide-containing gas and an injection facility 30 for fixing the recovered carbon dioxide into a stratum. The recovery and storage plant 3 is not limited to a configuration only for the fixation of carbon dioxide into a stratum. The recovery and storage plant 3 may be configured to perform enhanced oil recovery (EOR), that is, to inject carbon dioxide into an oil reservoir in order to efficiently recover crude oil.

In some embodiments, the injection facility 30 may include at least one compressor (compressors 31, 32, and 33 in FIG. 1, for example), and the carbon dioxide supply line 11 may be connected to a downstream side of the at least one compressor (any one of compressors 31, 32, and 33 in FIG. 1, for example) to supply the compressed carbon dioxide to the synthesis plant 10.

Figure 1:
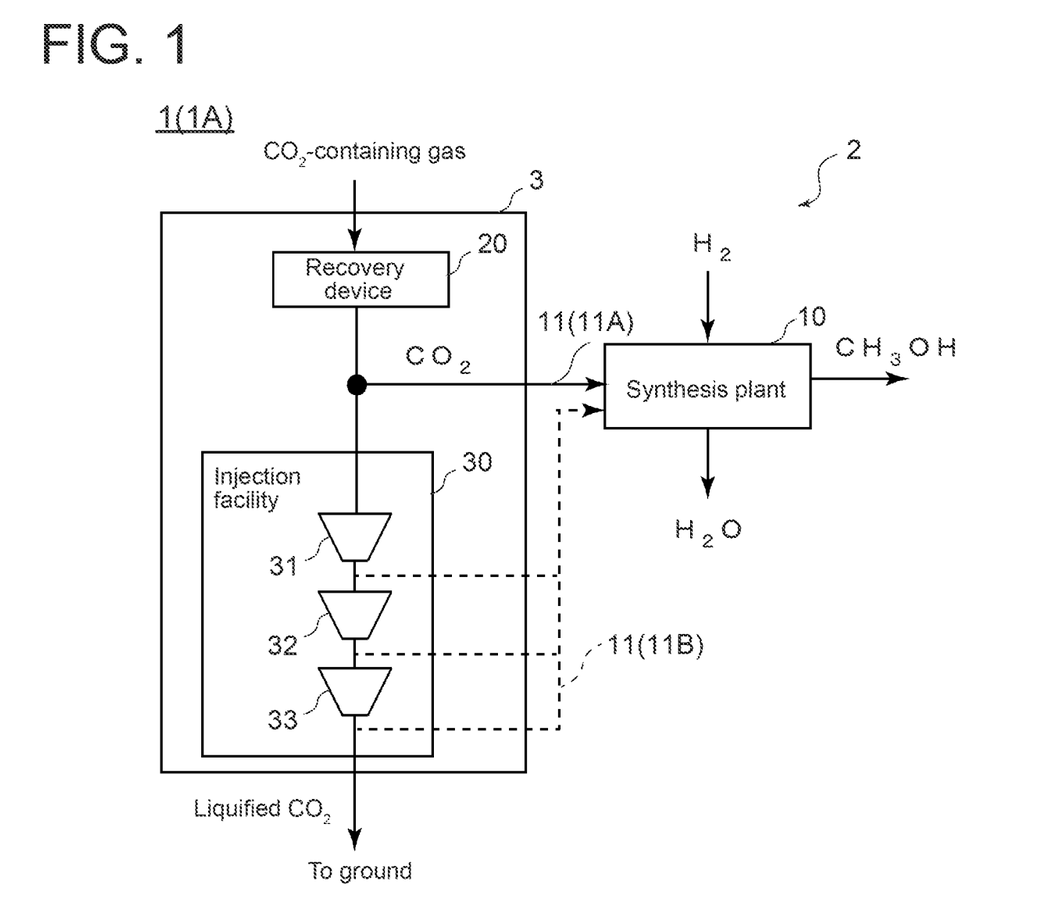
FIG. 1 is a schematic configuration diagram of a carbon dioxide treatment system according to an embodiment of the present disclosure.

The at least one compressor may be one compressor or a plurality of compressors (for example, three compressors 31, 32, 33 in FIG. 1). The carbon dioxide supply line 11 may be connected to a downstream side of a compressor (for example, compressor 31, 32, or 33 in FIG. 1) of the at least one compressor. In FIG. 1, three compressors 31, 32, and 33 are shown, but the number of compressors is not limited thereto.

In some embodiments, for example, as shown in FIG. 1, the injection facility 30 may include a plurality of compressors 31, 32, 33 connected in series, and the carbon dioxide supply line 11 (11B) may be connected to a passage for carbon dioxide in the injection facility 30 to supply carbon dioxide compressed by one or more compressors of the plurality of compressors 31, 32, 33 to the synthesis plant 10, as shown by the dashed line. In other words, carbon dioxide may be supplied to the synthesis plant 10 from the passage in the process of compression in multi-stage compression.

In some embodiments, for example, as shown in FIG. 4, the carbon dioxide treatment system 1 (1D) may include a raw material supply compressor 14 for compressing a hydrogen-containing gas at an upstream position in the synthesis plant 10, and the carbon dioxide supply line 11 may be connected to a position downstream of the raw material supply compressor 14 and upstream in the synthesis plant 10.

Figure 5:
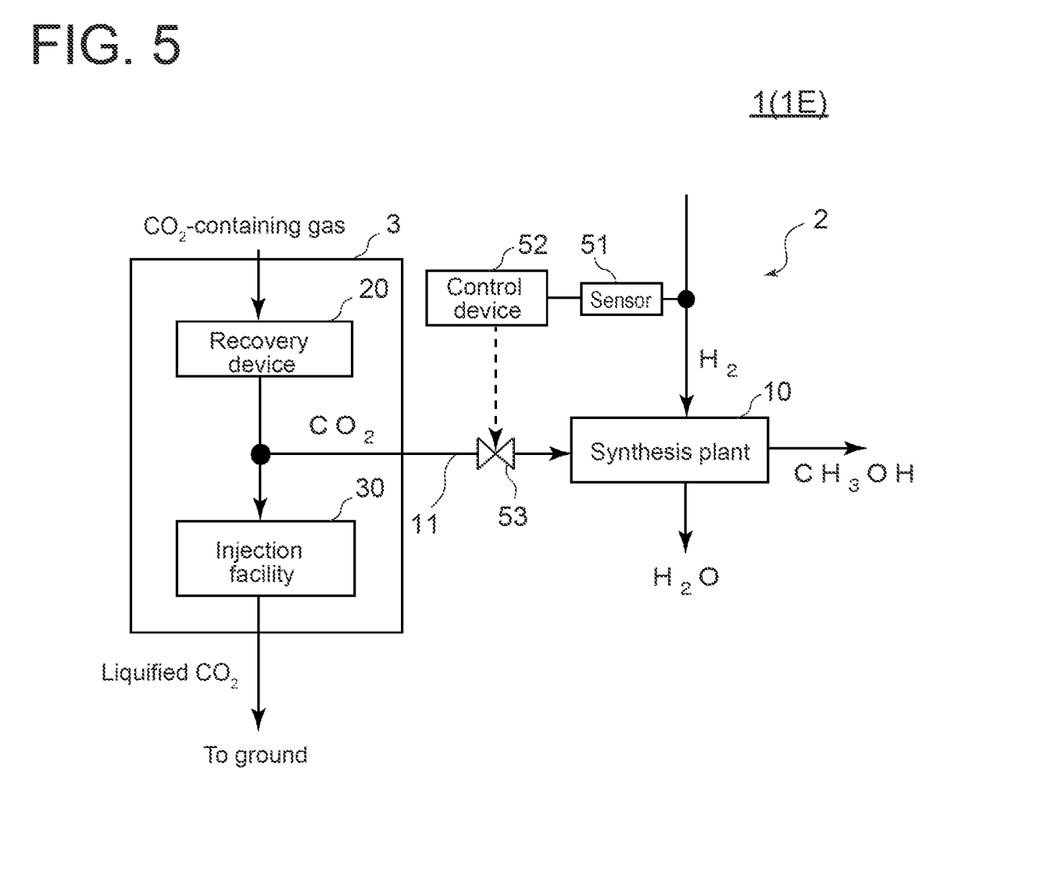
FIG. 5 is a schematic configuration diagram of a carbon dioxide treatment system according to an embodiment.

In some embodiments, for example, as shown in FIG. 5, the synthetic product production system 2 may include a sensor 51 for detecting the supply amount of the hydrogen-containing gas, a control device 52 configured to output an instruction according to the supply amount of the hydrogen-containing gas detected by the sensor 51, and a flow rate adjustment device 53 disposed in the carbon dioxide supply line 11 and configured to adjust the amount of carbon dioxide supplied to the synthesis plant 10 according to the instruction of the control device 52. For example, the flow rate adjustment device 53 may include a valve for adjusting the flow rate, and the control device 52 may control the opening degree of the valve through an instruction.

In some embodiments, for example, as shown in FIGS. 2 and 3, the carbon dioxide treatment system 1 (1B, 1C) may include a power generation facility 40 configured to generate power by combustion of an off-gas from the recovery device 20 of the recovery and storage plant 3, and an unreacted gas supply line 19 for supplying at least part of an unreacted gas (purge gas) discharged from the catalyst 16 of the synthesis plant 10 from a pipe for recirculating the unreacted gas to the power generation facility 40. The unreacted gas includes, for example, methane.

For example, as shown in FIG. 3, the carbon dioxide treatment system 1 may include a purge line 63 to be injected with a replacement gas during the shutdown period of the synthesis plant 10, and the unreacted gas supply line 19 may be connected to the purge line 63. For example, as shown in FIG. 3, the replacement gas is injected as indicated by the dotted arrow when valves 61, 62 are closed, and fills respective pipes downstream of the valves. For example, in the example shown in FIG. 3, the purge line 63 includes pipes from the valves 61, 62 to the gas-liquid separation device 17 and further includes a pipe for recirculating the unreacted gas (purge gas) The replacement gas is an inert gas (e.g., nitrogen gas).

In FIGS. 1 to 5, the carbon dioxide-containing gas supplied to the recovery device 20 may be an off-gas separated by the pressure swing adsorption (PSA) method in a refinery. The hydrogen-containing gas may be an off-gas from the recovery device 20 or a hydrogen-containing gas produced by using by-product hydrogen or renewable energy.

Conclusion

The contents described in the above embodiments would be understood as follows, for instance.

(1) A synthetic product production system (2) according at least one embodiment of the present disclosure comprises: a synthesis plant (10) for producing a synthetic product by synthesizing a hydrogen-containing gas and carbon dioxide; and a carbon dioxide supply line (11) for supplying the carbon dioxide to the synthesis plant (10) from a recovery and storage plant (3) including a recovery device (20) for recovering the carbon dioxide from a carbon dioxide-containing gas and an injection facility (30) for fixing the recovered carbon dioxide into a stratum.

The facility for storing carbon dioxide (e.g., the recovery and storage plant 3) has to be installed in a place where carbon dioxide can be stored, and there are restrictions on the installation location in contrast to the facility for utilizing carbon dioxide for the production of the synthetic product (e.g., the synthesis plant 10 configured to produce the synthetic product). Therefore, combining these facilities has not been considered.

However, the facility for storing carbon dioxide is provided with a carbon dioxide recovery device (20). The amount of carbon dioxide used for the synthesis is smaller than the amount of carbon dioxide injected. If the facility for utilizing carbon dioxide for the production of the synthetic product (e.g., the synthesis plant 10 configured to produce the synthetic product) is provided with a dedicated carbon dioxide recovery device (20) for such a small amount of carbon dioxide, the facility cost increases. As a result, the unit cost of the synthetic product also increases. In this regard, according to the configuration described in (1), since the synthesis plant (10) uses carbon dioxide recovered by the recovery and storage plant (3), the carbon dioxide recovery device (20) dedicated to the synthesis plant (10) can be eliminated.

(2) In some embodiments, in the above configuration (1), the injection facility (30) includes at least one compressor (e.g., any one of compressors 31, 32, 33), and the carbon dioxide supply line (11) is connected to a downstream side of the at least one compressor (e.g., any one of compressors 31, 32, 33) to supply the carbon dioxide compressed to the synthesis plant (10).

If the synthesis plant (10) is provided with a dedicated carbon dioxide compressor (31, 32, 33) for a small amount of carbon dioxide, the facility cost increases. In this regard, according to the configuration described in (2), since the synthesis plant uses carbon dioxide compressed by the compressor (e.g., compressor 31, 32, 33) of the injection facility (30), the carbon dioxide compressor (31, 32, 33) dedicated to the synthesis plant (10) can be eliminated.

(3) In some embodiments, in the above configuration (1), the injection facility (30) includes a plurality of compressors (e.g., compressors 31, 32, 33) connected in series, and the carbon dioxide supply line (11) is connected to a passage for the carbon dioxide in the injection facility (30) to supply the carbon dioxide compressed by one or more compressors of the plurality of compressors (e.g., one or more of compressors 31, 32, 33) to the synthesis plant (10).

If the synthesis plant (10) is provided with a dedicated carbon dioxide compressor (31, 32, 33) for a small amount of carbon dioxide, the facility cost increases. In this regard, according to the configuration described in (3), since the synthesis plant uses carbon dioxide compressed by the compressor (e.g., compressor 31, 32, 33) of the injection facility (30), the carbon dioxide compressor (31, 32, 33) dedicated to the synthesis plant (10) can be eliminated.

Further, in the configuration described in (3), the compressors (e.g., compressor 31, 32, 33) are configured to perform multi-stage compression in the injection facility (30). By selecting a position where carbon dioxide has an appropriate pressure in the carbon dioxide passage after or during compression by these compressors (e.g., compressors 31, 32, 33) and connecting the carbon dioxide supply line (11) to the selected position, carbon dioxide compressed to a pressure suitable for the production of the synthetic product can be supplied to the synthesis plant (10).

(4) In some embodiments, in the above configuration (2) or (3), the synthetic product production system (2) comprises a raw material supply compressor (14) for compressing the hydrogen-containing gas at an upstream position in the synthesis plant (10). The carbon dioxide supply line (11) is connected to a position downstream of the raw material supply compressor (14) and upstream in the synthesis plant (10).

According to the configuration described in (4), a mixture containing compressed carbon dioxide and hydrogen can be supplied to the synthesis plant (10) without providing a compressor for compressing carbon dioxide used for the synthesis on the upstream side of the synthesis plant (10).

(5) In some embodiments, in any one of the above configurations (1) to (4), the synthetic product production system comprises: a sensor (51) for detecting a supply amount of the hydrogen-containing gas, a control device (52) configured to output an instruction according to the supply amount of the hydrogen-containing gas detected by the sensor (51), and a flow rate adjustment device (53) disposed in the carbon dioxide supply line (11) and configured to adjust an amount of the carbon dioxide supplied to the synthesis plant (10) according to the instruction of the control device (52).

In some cases, the recovery amount of carbon dioxide tends to be large due to enormous carbon dioxide emissions, while the supply amount of hydrogen-containing gas is small. In addition, if the hydrogen-containing gas is byproduct hydrogen discharged as a byproduct from another plant or a gas generated by water electrolysis using renewable energy, the supply amount of the hydrogen-containing gas may fluctuate. In such cases, the amount of the synthetic product produced by the synthesis plant (10) depends on the supply amount of the hydrogen-containing gas, and a surplus may be generated in the recovery amount of carbon dioxide. In this regard, according to the configuration described in (5), the flow rate distribution of carbon dioxide can be adjusted so that carbon dioxide is supplied to the synthesis plant (10) in an amount necessary for producing the synthetic product according to the supply amount of the hydrogen-containing gas while unnecessary carbon dioxide is injected. Therefore, the operability of the system is improved, and even if a surplus is generated in the recovered carbon dioxide, it can be prevented from being released to the atmosphere.

(6) In some embodiments, in any one of the above configurations (1) to (5), the synthesis plant (10) is configured to produce at least one of methanol, methane, or dimethyl ether as the synthetic product.

According to the configuration described in (6), it is advantageous because a synthetic product excellent in storage stability as compared with hydrogen gas is produced.

(7) A carbon dioxide treatment system (1) according to at least one embodiment of the present disclosure comprises: the synthetic product production system (2) according to any one of the above configurations (1) to (6); a recovery and storage plant (3) including a recovery device (20) for recovering carbon dioxide from a carbon dioxide-containing gas and an injection facility (30) for fixing the recovered carbon dioxide into a stratum; a power generation facility (40) configured to generate power by combustion of an off-gas from the recovery device (20) of the recovery and storage plant (3); and an unreacted gas supply line (19) for supplying at least part of a discharged unreacted gas from a pipe for recirculating the unreacted gas to the power generation facility (40).

Since it is difficult to react all of the supplied carbon dioxide and hydrogen at once, the synthesis plant (10) is usually provided with a pipe for recirculating the unreacted gas. On the other hand, when the unreacted gas is recirculated, an inert gas accumulates in the unreacted gas, and the reaction efficiency decreases. Therefore, it is necessary to partially remove the unreacted gas from the system. According to the configuration described in (7), since the unreacted gas is taken out from the pipe, and combustible components such as methane contained in the unreacted gas are supplied as fuel for the power generation facility, the energy efficiency of the entire system can be improved.

(8) In some embodiments, in the above configuration (7), the carbon dioxide treatment system (2) comprises a purge line (63) to be injected with a replacement gas during a shutdown period of the synthesis plant (10). The unreacted gas supply line (19) is connected to the purge line (63).

In a configuration in which a replacement gas (e.g., inert gas) is injected during the shutdown period of the synthesis plant (10), and then the replacement gas is purged with the hydrogen-containing gas at the restart, the mixture of the hydrogen-containing gas and the replacement gas is usually discarded. In this regard, according to the configuration described in (8), since such a mixture is not discarded but used as fuel, the energy efficiency of the entire system can be improved.

REFERENCE SIGNS LIST

1 Carbon dioxide treatment system
2 Synthetic product production system
3 Recovery and storage plant
10 Synthesis plant
11 Carbon dioxide supply line
12, 13 Purification device
14 Raw material supply compressor
15, 31 Compressor
16 Catalyst
17 Gas-liquid separation device
18 Distillation device
19 Unreacted gas supply line
20 Recovery device
30 Injection facility
40 Power generation facility
51 Sensor
52 Control device
53 Flow rate adjustment device
61, 62 Valve
63 Purge line

The invention claimed is:

1. A synthetic product production system, comprising:
a synthesis plant for producing a synthetic product from a hydrogen-containing gas and carbon dioxide; and
a carbon dioxide supply line for supplying the carbon dioxide to the synthesis plant, the carbon dioxide supply line being configured to extract and supply a first stream of the carbon dioxide to the synthesis plant from a recovery and storage plant including a recovery device for recovering the carbon dioxide from a carbon dioxide-containing gas and an injection facility for fixing a second stream of the recovered carbon dioxide into a stratum,
wherein the injection facility includes at least one compressor, and
wherein the carbon dioxide supply line is connected to a downstream side of the at least one compressor to supply the second stream of the carbon dioxide compressed to the synthesis plant.

2. The synthetic product production system according to claim 1,
wherein the at least one compressor includes a plurality of compressors disposed in series on a passage for the carbon dioxide in the injection facility, and
wherein the carbon dioxide supply line is connected to the passage for the carbon dioxide in the injection facility to supply the first stream of the carbon dioxide compressed by one or more compressors of the plurality of compressors to the synthesis plant.

3. The synthetic product production system according to claim 1, comprising a raw material supply compressor for compressing the hydrogen-containing gas at an upstream position in the synthesis plant,
wherein the carbon dioxide supply line is connected to a position downstream of the raw material supply compressor and upstream in the synthesis plant.

4. The synthetic product production system according to claim 1, comprising:
a sensor for detecting a supply amount of the hydrogen-containing gas;
a control device configured to output an instruction according to the supply amount of the hydrogen-containing gas detected by the sensor; and
a flow rate adjustment device disposed in the carbon dioxide supply line and configured to adjust an amount of the first stream of the carbon dioxide supplied to the synthesis plant according to the instruction of the control device.

5. The synthetic product production system according to claim 1,
wherein the synthesis plant is configured to produce at least one of methanol, methane, or dimethyl ether as the synthetic product.

6. A carbon dioxide treatment system, comprising:
a recovery and storage plant including a recovery device for recovering carbon dioxide from a carbon dioxide-containing gas and an injection facility for fixing the recovered carbon dioxide into a stratum;
a synthesis plant for producing a synthetic product from a hydrogen-containing gas and carbon dioxide;
a carbon dioxide supply line configured to extract and supply a first stream of the carbon dioxide to the synthesis plant from the recovery and storage plant, the first stream of the carbon dioxide being different from a second stream of the carbon dioxide to be injected to the stratum;
a power generation facility configured to generate power by combustion of an off-gas generated from the recovery device of the recovery and storage plant; and
an unreacted gas supply line for extracting and supplying at least part of a discharged unreacted gas generated from the synthesis plant via a pipe provided in the synthesis plant for recirculating the unreacted gas to the power generation facility.

7. The carbon dioxide treatment system according to claim 6, comprising a purge line to be injected with a replacement gas during a shutdown period of the synthesis plant,
   wherein the unreacted gas supply line is connected to the purge line.

* * * * *